United States Patent [19]
Rothchild

[11] Patent Number: 5,672,197
[45] Date of Patent: Sep. 30, 1997

[54] GAS SEPARATION BY CONTINUOUS PRESSURE-SWING CHROMATOGRAPHY

[76] Inventor: Ronald D. Rothchild, 1 Leah La., Plainview, N.Y. 11803

[21] Appl. No.: 540,890

[22] Filed: Oct. 11, 1995

[51] Int. Cl.$^6$ ................................................. B01D 53/047
[52] U.S. Cl. ........................ 95/98; 95/103; 95/105; 95/130; 95/138
[58] Field of Search ...................... 95/86, 95–105, 95/107, 138; 96/108, 121–124

[56] References Cited

U.S. PATENT DOCUMENTS

| | | | |
|---|---|---|---|
| Re. 29,941 | 3/1979 | Bird | 95/98 X |
| 1,617,305 | 2/1927 | Guyer et al. | 95/95 |
| 3,155,468 | 11/1964 | de Montgareuil et al. | 95/103 |
| 3,728,843 | 4/1973 | Nagy et al. | 95/96 |
| 3,992,175 | 11/1976 | Klementi et al. | 95/86 |
| 4,001,112 | 1/1977 | Barker et al. | 95/86 X |
| 4,402,832 | 9/1983 | Gerhold | 95/86 X |
| 4,478,721 | 10/1984 | Gerhold | 95/86 X |
| 4,498,991 | 2/1985 | Oroskar | 95/86 X |
| 4,612,022 | 9/1986 | Berry | 95/138 X |
| 5,112,367 | 5/1992 | Hill | 95/98 |
| 5,487,775 | 1/1996 | LaCava et al. | 95/98 |

OTHER PUBLICATIONS

Koichi Mikami et al., "PSA System of Producing High Aurity M2Gas", Mitsui Zousen Engineering Reports, No. 137, pp. 44–49, 1989.

Michinobu Takemura et al., "Scale Up of Nirogen Generator", R–D Kobe Steel Engineering Reports, vol. 39, No. 1, pp. 101–104, 1989.

Primary Examiner—Robert Spitzer

[57] ABSTRACT

A process for separating a mixture of gases by selective adsorption, in which pressure swing is used to induce both desorption and the flow of gas through at least one simulated moving chromatographic column.

12 Claims, 3 Drawing Sheets

SIMULATION SUMMARY

SIMULATED CONDITIONS

| | | 1 BED LONG, BED REPLACED | 2 BEDS LONG, MOVING COLUMN | 3 BEDS LONG, MOVING COLUMN |
|---|---|---|---|---|
| PRODUCT ENRICHMENT ZONE | | | | |
| TOTAL BEDS IN SYSTEM | | 4 | 5 | 6 |
| TOTAL ADSORBENT INVENTORY | | 200 FT$^3$ | SAME | SAME |
| FEEDSTOCK AIR RATE | | 16,800 SCFH | SAME | SAME |
| OPERATING PRESSURE (ADSORPTION) | | 1.2 BAR | SAME | SAME |
| LOWER PRESSURE (DESORPTION) | | 0.065 BAR | SAME | SAME |
| BED SWITCHING INTERVAL | | 30 SECONDS | 24 SECONDS | 20 SECONDS |
| OVERALL SYSTEM CYCLE TIME | | 2 MINUTES | SAME | SAME |
| PRODUCT PRESSURE | | 1 BAR | SAME | SAME |
| NITROGEN PRODUCTION RATE | SERIES A | 12,000 SCFH | SAME | SAME |
| | SERIES B | 11,500 SCFH | SAME | SAME |
| NITROGEN YIELD | SERIES A | 90% | SAME | SAME |
| | SERIES B | 86% | SAME | SAME |

RESULTS

| | | | | |
|---|---|---|---|---|
| PRODUCT PURITY AND (PPM O$_2$) | SERIES A | 99.7% (3,000 PPM) | 99.997% (24 PPM) | 99.99998% (.15 PPM) |
| | SERIES B | 99.8% (1,700 PPM) | 99.9998% (2 PPM) | 99.9999998% (2 PPB) |

FIGURE 3

GAS SEPARATION BY CONTINUOUS PRESSURE-SWING CHROMATOGRAPHY

BACKGROUND OF THE INVENTION

This invention relates to separation of mixed gases. More particularly, this invention relates to methods and apparatus to separate gases by adsorption with improved performance and economy.

Cryogenic separation of mixed gases such as air provides a high degree of purity, such as nitrogen with less than 10 ppm oxygen as an impurity, with high efficiency and low operating costs. However the plant and equipment to cryogenically separate air is expensive and practical only on a very large scale.

On smaller scale, processes based on adsorption can be attractive because of substantially lower capital investment. However adsorption processes for gas separation have been much less efficient and more expensive to operate, especially if high product purity is an objective.

For example in generating high purity nitrogen from air by pressure swing adsorption (or "PSA", including the special case of "vacuum swing" adsorption, "VSA"), yield, i.e. nitrogen recovery from the feedstock air, is a small fraction of feedstock volume, but power consumption and operating cost are determined by the total amount of feedstock air processed.

This has been true even where multiple adsorption beds are used since, even with multiple beds, a substantial portion of the gas component desired as product is exhausted as impure waste when the beds are regenerated. In some cases the multiple beds constitute essentially identical and independent systems in parallel, operated in a phased manner to render the inherently "batch" process somewhat more continuous in product flow. Each bed contributes to capacity but process performance expressed as product purity and yield is not substantially greater with many beds than with few. The whole is not greater than the sum of the parts. Examples include U.S. Pat. No. 5,403,385, U.S. Pat. No. 5,354,346, U.S. Pat. No. 5,346,535, U.S. Pat. No. 5,261,947, U.S. Pat. No. 5,250,088, U.S. Pat. No. 5,246,676, U.S. Pat. No. 5,203,888, U.S. Pat. No. 5,176,722, U.S. Pat. No. 5,163,978, U.S. Pat. No. 5,122,164, U.S. Pat. No. 5,042,995, U.S. Pat. No. 5,002,591, U.S. Pat. No. 4,959,083, U.S. Pat. No. 4,954,146, U.S. Pat. No. 4,913,709, U.S. Pat. No. 4,816,039, U.S. Pat. No. 4,576,614, U.S. Pat. No. 4,522,637, U.S. Pat. Nos. 4,194,891 and 890, U.S. Pat. No. 4,168,149, U.S. Pat. Nos. 4,144,038 and 037, and U.S. Pat. No. 4,042,349. U.S. Pat. No. 4,834,780 describes a six-adsorber PSA process in which the six adsorbent beds operate substantially independently but staggered, with only one bed at a time in an adsorption mode.

Simulated moving bed (SMB) processes, in which a solid adsorbent is made to effectively move in the direction countercurrent to internal fluid flow, have also been used for separations in a form of continuous chromatography.

Examples are described in U.S. Pat. Nos. 4,478,721, 4,498,991 and 5,387,347.

These examples are typical of many in that a circulating desorbent is required, to act as a carrier fluid for the components being separated and to regenerate the adsorbent. In principle the SMB processes can be applied to gases, and have been, but application has been limited.

The article entitled *Counter-Current and Simulated Counter-Current Adsorption Separation Processes*, by Ruthven and Ching, in Chemical Engineering Science (Vol. 44, No. 5, pp. 1011–1038, 1989) indicates that the desorption or regeneration step ". . . may involve either near-isothermal displacement or thermal swing operation in which the desorption section runs at elevated temperature." Examples are provided of SMB operation with gases such as pure nitrogen or isopropyl benzene vapor used, as a desorbent and carrier fluid, in the separation of gaseous components.

In the textbook entitled *Gas Separation by Adsorption Processes*, published by Butterworths, author Ralph T. Yang states, "The simulated moving-bed processes, under the general name of Sorbex, are restricted to liquids and apparently are not competitive with the pressure-swing adsorption process for gas-phase applications . . ."

Exceptions are cited, but the utility of SMB chromatography for separating gases has been limited by the need for a carrier and desorbent gas.

SUMMARY OF THE INVENTION

An array of beds connected in series, packed with a pressure-sensitive selective adsorbent material, is operated in the manner of continuous simulated moving bed chromatography, with adsorbent effectively moving countercurrent and upstream with respect to internal gas flow. However no desorbent is used. Instead, internal gas flow is manipulated such that the function of a desorbent and carrier fluid is simulated by an effective co-current flow of vacuum as a pseudo-fluid, so that gas is at least partially displaced by vacuum at the upstream end of the array of beds, and displaces vacuum at the downstream end of the array.

The array is organized to include at least one simulated moving chromatographic column, in the product enrichment zone between the feedstock inlet port and the primary product outlet port. Preferably the array includes two simulated moving columns, one upstream and one downstream with respect to the feedstock inlet port.

Thus a method is provided, combining simulated moving bed chromatography with pressure swing adsorption and referred to as pressure swing chromatography, for separating gases by selective adsorption, in which pressure swing is used to induce both desorption and the flow of gas through at least one simulated moving chromatographic column. The method provides high product purity combined with high efficiency, with product yield approaching 100%.

BRIEF DESCRIPTION OF THE DRAWINGS

FIG. 3 is a Table showing a comparison of simulation results for topologically similar methods, with and without a moving extract enrichment column, and with varying size columns and process conditions.

DETAILED DESCRIPTION AND PREFERRED EMBODIMENTS

Figure 1:
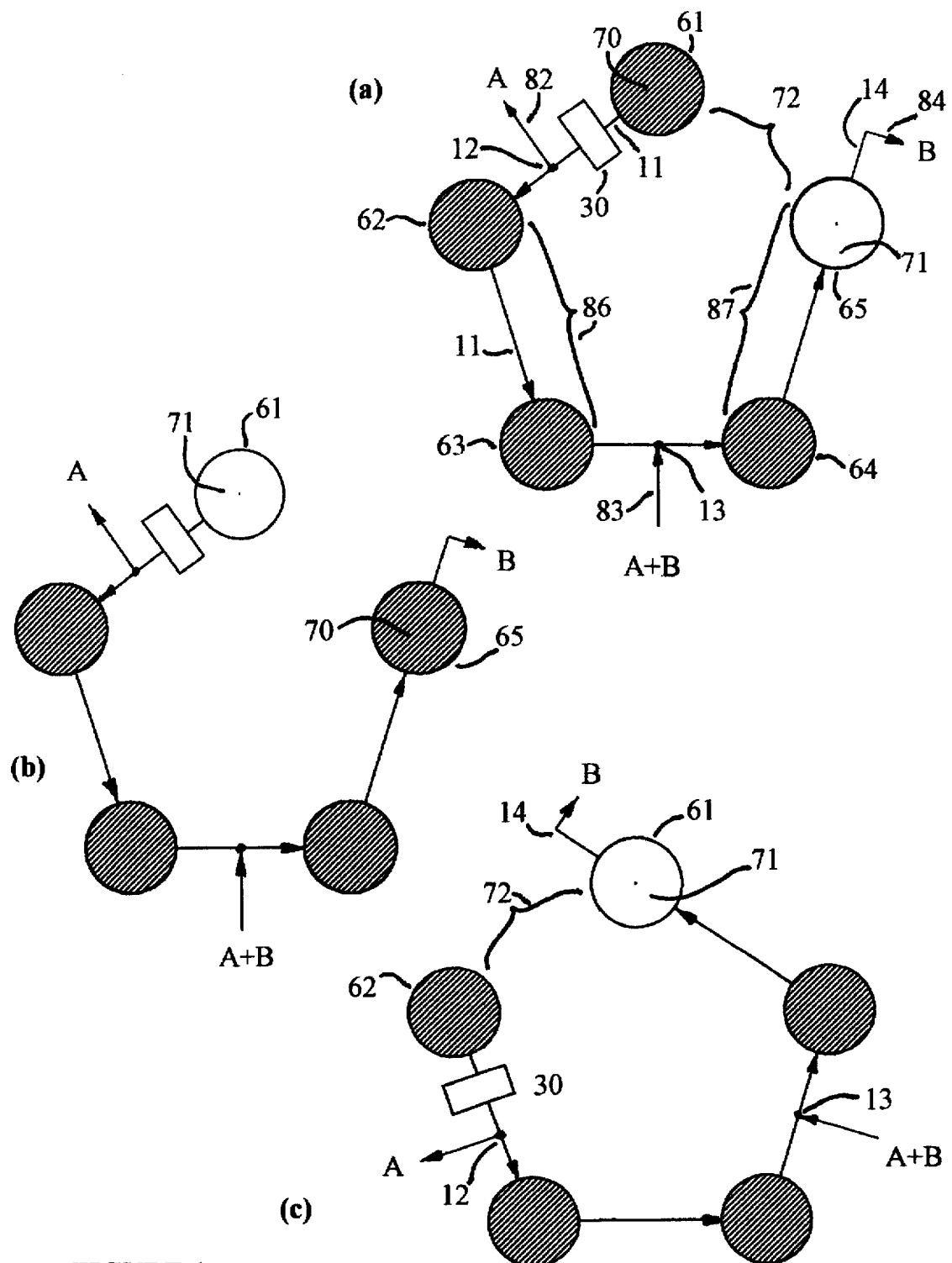
FIG. 1, *a*, *b* and *c*, is a schematic diagram of a five-bed system with two simulated moving columns, illustrating gas and effective adsorbent flows.

The present invention is a method and associated apparatus for using a pressure-dependent selective gas adsorbing medium, such as those used in PSA or VSA gas separation systems, to make an efficient chromatographic separation of a mixture of gases. A mixed feed containing two components, denoted A and B, may be separated into two products; an extract product containing mainly A (the more strongly adsorbed species, or group of species with similarly strong adsorption properties), and a raffinate containing mainly B (the less strongly adsorbed species or group of species).

The method is inherently continuous in nature, though internally cyclical. Feedstock may be added and product withdrawn continuously except for the substantially instantaneous interval while switching valves are being opened and shut.

An internal gas flow is pumped through a plurality of beds in fluid conmmunication in a series, each bed containing a pressure dependent adsorbent packing. At the beginning of a cycle all the beds, except the one in the most downstream position with respect to the internal gas flow, are at operating pressure at which the packing is an effective and selective adsorbent for the mixture. The most downstream bed is at a lower pressure at which relatively little gas is adsorbed. During the cycle:

Gas is pumped from the most upstream bed in the series to generate the internal gas flow and displace gas through the series in the downstream direction.

An extract product A is withdrawn as a first outlet flow of gas from a first outlet port in fluid communication with the most upstream bed in the series.

A feedstock flow of mixture A and B is added to the series of beds through an inlet port located downstream from the first outlet port.

A raffinate product B is withdrawn as a second outlet flow, from a second outlet port in fluid communication with the most downstream bed in the series.

By the end of a cycle, gas pressure in the most downstream bed is increased to operating pressure, while pressure in the most upstream bed is reduced to the lower pressure. At the end of a cycle, switching valves are used to switch the positions of ports and other bed connections, so that each bed effectively advances upstream with respect to the internal gas flow by one position, except for the most upstream bed, which is effectively moved to the most downstream position.

Both the most upstream and the most downstream beds are subject to pressure swings during the operating cycle; from operating to lower pressure and from lower to operating pressure, respectively. Other beds, between the most upstream and most downstream, are at operating pressure throughout the cycle.

The series includes at least one simulated moving chromatographic column, preferably located in a product enrichment zone, which is the region between the inlet port and primary product outlet port. The inlet port and the other outlet port are also separated, by at least one bed. Preferably the series includes two simulated moving columns; one upstream and one downstream of the inlet port so that the inlet port constitutes the boundary between the two simulated moving columns.

A simulated moving column must contain two or more beds. Periodically the most upstream bed of the column, which has been fully enriched or saturated, is removed from the column. It is replaced in its position by the other beds in the column advancing upstream by an increment of one bed, and the most downstream bed of the column is replaced in its position by a fresh bed.

This has the advantage that product can be drawn from only an optimal end portion of the column, for high purity, without losing the product in the remainder of the column. Effectively the product outlet port follows (if extract) or leads (if raffinate) the axial concentration wavefront in the column.

In contrast, if only one bed is present between the inlet and outlet port, it does not undergo simulated motion but is simply replaced when the beds are switched. If product is drawn only from the far end of the moving concentration wavefront, e.g. if beds are switched and the enrichment bed moved away when only a small portion of that wavefront is within it, to obtain high purity, then product yield will be extremely low and much product will be lost.

Figure 2:
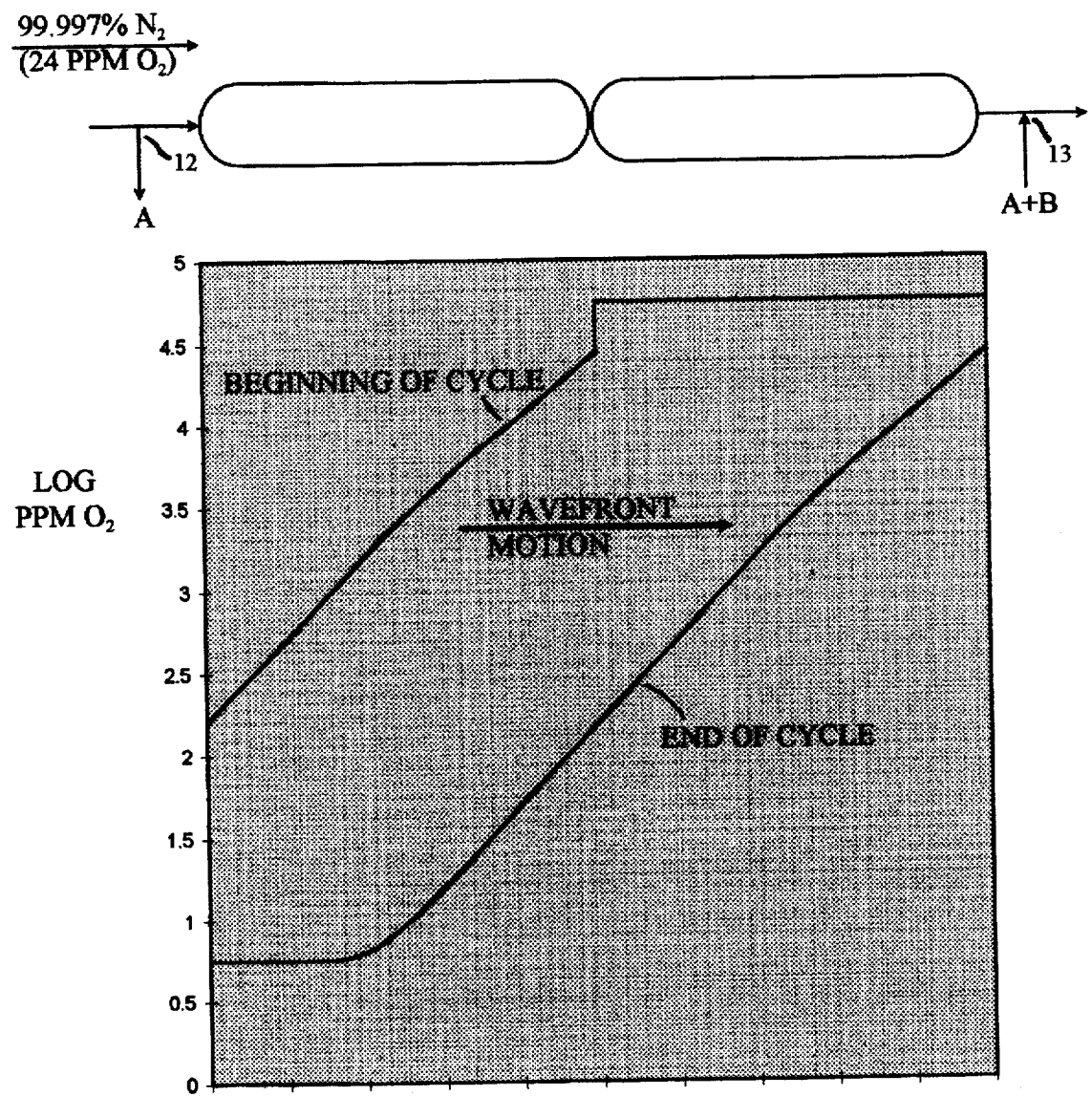
FIG. 2 is a diagram showing typical axial raffinate concentration profiles within the extract enrichment column, at the beginning and end of a switching cycle, in a simulation of the preferred embodiment.

The significance of concentration wavefront position when the beds are switched is illustrated in FIG. 2, which is discussed in greater detail in connection with the preferred embodiment. The size of the upstream portion of the column which is removed when beds are switched, and of the increment of column motion, is the fraction 1/N of the column, where N is the number of beds in the column. The maximum increment of column motion that can be provided, that permits exploiting the effect of wavefront position, is ½ column. Simulations described below indicate that much more extreme product purity, with the same high yield, is obtainable if the increment of column motion is ⅓ column or less.

In accordance with the present invention, each additional bed necessarily becomes part of a simulated moving chromatographic column, increasing the number N of beds in that column and further reducing the fraction 1/N of the column that is removed when beds are switched. Therefore each additional bed increases product purity and yield as well as production capacity and, in contrast with prior art multiple bed systems that are essentially parallel in organization, the whole is greater than the sum of the parts.

If the configuration is to be optimized for a single product, it may sometimes be economical to locate all but one bed on one side, either upstream or downstream depending on which outlet flow is product, of the inlet port. Preferably, the more highly adsorbed species will be the desired product, which will then be drawn as extract.

For example in producing nitrogen from air, using a zeolite adsorbent which preferentially adsorbs nitrogen, it may be economical to position the inlet port with most beds upstream and only one downstream. This will lead to lower yield and higher operating costs than if a downstream moving column were provided, but with lower equipment cost due to one less bed required.

It is not necessary to completely evacuate the most upstream bed. However any residual gas left in that bed at the end of a cycle may reduce purity of the raffinate. Also, the residual gas will reduce the production rate of pure extract per unit volume of adsorbent. The level of the lower pressure is therefore a compromise, between the cost of drawing high vacuum and the cost incurred as a result of residual gas in the bed when switched.

The first outlet port may be in fluid communication with, and extract A drawn from, either end of the most upstream bed (or even, conceivably, a location within the bed). Similarly, raffinate B may be drawn from either end of the most downstream bed, though the downstream end is preferred.

Also, it should be understood that ports in communication with the series of beds may be in such commnunication through valves, controls, pumps or compressors and the like, as appropriate, to obtain the required process flows.

Operation of the process will be further understood by reference to FIG. 1 which shows a configuration with five beds, 61, 62, 63, 64 and 65, with three beds upstream and two beds downstream of inlet port 13. Beds 62 and 63 in FIG. 1a comprise a first simulated moving chromatographic column 86, and beds 64 and 65 comprise a second simulated moving chromatographic column 87.

FIG. 1a shows conditions at the beginning of a cycle. Beds 61 through 64 contain gas at relatively elevated operating pressure 70, indicated by crosshatching. Bed 65 contains gas at relatively lower pressure 71. Bed 61 is in fluid communication with bed 62 through pump means 30 and conduit means 11. Bed 62 is in fluid communication with bed 63, 63 with 64, and 64 with 65. However bed 65 is not in fluid communication with bed 61, causing effective dead end 72 between those two beds.

During the cycle gas is displaced through the bed series by pump means 30, from bed 61 and toward bed 65. Meanwhile a flow 82 of extract product A is drawn from first outlet port 12, a flow 84 of raffinate product B is drawn from second outlet port 14, and a flow 83 of feedstock is added through inlet port 13.

Referring to FIG. 1, at the end of a cycle but before bed switching, bed 61 contains gas at relatively lower pressure 71 while bed 65 contains gas at operating pressure 70.

Well known switching valve means are then used to advance pump means 30, ports 12, 13 and 14, and dead end 72, by one bed following the direction of internal gas flow so that dead end 72, for example, is now between beds 61 and 62, illustrated in FIG. 1c. In this way, each bed has effectively advanced in the direction counter to internal gas flow. Bed 62, for example, which had been adjacent the most upstream bed, is now the most upstream bed. The bed containing relatively lower pressure 71 is again the most downstream bed, and initial cycle conditions are restored.

FIG. 2 shows the simulated axial oxygen concentration in the two beds that constitute the moving chromatographic column between ports 12 and 13, in the system illustrated schematically in FIG. 1 as applied to the production of nitrogen from air. Simulated process conditions are as indicated in the Table of FIG. 3.

The simulated bed switching interval is 24 seconds, which corresponds to a switching valve and overall system cycle time of two minutes. Power consumption is approximately 60 kw, which corresponds to unit power consumption of approximately 0.5 kw-hr/CCF product, with product at 1 bar. The adsorbent is a commercially available zeolite material with bulk density 37 lb/ft$^3$ that typically adsorbs 0.5% to 1.5% its weight in gas at atmospheric pressure; for the purpose of simulation, adsorbed gas is 0.5% of the zeolite weight.

Product nitrogen purity resulting from simulation of the preferred embodiment in these conditions is 99.997%, which corresponds to 24 ppm of impurities. Simulated process conditions and results are summarized in the Table of FIG. 3, which compares the preferred embodiment to two alternatives; one without a moving chromatographic column, with only one bed in the product enrichment zone, and one with a larger column than the preferred embodiment.

Simulation results clearly illustrate that process performance, in this case product purity with yield invariant, correlates strongly with the presence and size of the moving column. These three simulations, all with 90% yield as a condition, are denoted Series A in the Table of FIG. 3.

The advantage of the simulated moving column is further clarified by simulating the system's response to a reduction of nitrogen yield to 86%, with all other process conditions held constant. These simulations are denoted Series B in the Table of FIG. 3.

Product purity in the preferred embodiment is increased to 99.9998 (2 ppm impurities). In both simulations which include a moving column, the slight yield reduction leads to improved product purity by an order of magnitude or more. However product purity from the system without a moving column increases only modestly. Much greater benefit accrues, when the concentration wavefront is allowed to move slightly further downstream before bed switching, if the product enrichment zone is a moving column.

Moreover the simulated moving column permits more complete purging. The initial condition of a bed moving into position between the product and inlet ports, from a former position downstream of the inlet port, will be about 95% nitrogen. With one bed between those two ports, it is purged once and then, at the end of a switching cycle, moved upstream to be stripped.

With a column of N beds, each of them is purged N times, each time with product gas of higher purity. However there is no increase in the amount of nitrogen used or needed for purging. Rather, the same purge gas is used N times, being each successive time less pure but substantially more relatively pure than the bed it is purging. Therefore, as the simulation illustrates in the relative performance of different configurations, the moving column yields a very substantial improvement in product purity, with a modest increase in equipment complexity and essentially no increase in operating cost.

The two-bed moving column has been described as preferred because it will serve in appropriate applications at very low cost and is the simplest embodiment for the purpose of explanation. The three-bed moving column is further preferred. It will efficiently yield nitrogen comparable to the highest purity cryogenically produced liquid, at a cost only marginally higher than the two-bed column and still very low compared with that of the cryogenic product.

The locations of compressors, vacuum pumps and the like may be varied as practical as long as the desired flows are obtained. Moreover, the drawing of outlet flows and addition of feedstock may be assisted by separate pump means and include accumulators as required, depending on the details of configuration.

An expander may be included to recover energy from gas that is, for example, being transferred from higher to lower pressure, e.g. into the most downstream bed. Also, provision may be made to heat or cool flowing gas as needed, to maintain a stable temperature in the beds.

Those beds which are at operating pressure need not all be at the same pressure, though having them all at substantially the same pressure leads to the simplest process and operation. Alternatively, higher purity may be obtained by maintaining gas velocity, instead of pressure, uniform over those beds that are at operating pressure, i.e. a high enough pressure for the adsorbent to be effective.

The amounts of extract A and raffinate B drawn from first and second outlet ports will be substantially similar to the amounts of A and B present in the feedstock. However these outlet stream amounts may be modified slightly to enhance performance. For example, making product streams A and B slightly smaller and larger, respectively, leads to higher purity of extract product stream A. This is the way the position of the concentration wavefront, at the time of bed switching, is controlled.

Extract and raffinate streams A and B may be drawn over the entire cycle or during only a portion of the cycle, such as at the beginning or end, for example to reduce power consumption or improve product purity. For example, referring again to FIG. 3, raffinate stream 84 may be drawn toward the end of the cycle, when the pressure in the most downstream bed 64 has been increased to operating pressure. However flow in the moving column should preferably be maintained continuous. The method is inherently continuous, though intermittent flows may be imposed by controls where advantageous.

The process as described is primarily and best suited for binary separations as has been illustrated. However in a manner analogous to practice in liquid separations, additional ports and beds may be provided where separation of more than two components is desired, e.g. as in the production of separate streams of sucrose, invert, and non-sugars, from cane molasses.

Performance of the invention has been described in connection with the separation of air to produce pure nitrogen. However it should be understood that the invention can be applied to separation of any gas mixture for which an appropriate selective adsorbent exists, such as, for example, oxygen and argon. In connection with separation of other gases; adsorbent selectivity differences may not be as great as between nitrogen and oxygen. Moving chromatographic columns of three or more beds may be necessary rather than preferred.

Air is a unique feedstock, too, in that it is free except for the cost of processing it and its components are environmentally acceptable. These characteristics of air provide design freedom that will not necessarily exist when separating other gases.

While the invention has been described in connection with the preferred embodiments, it is not intended to limit the invention to the particular forms set forth but, on the contrary, it is intended to cover such alternatives, modifications and equivalents as may be included within the spirit and scope of the invention as defined by the appended claims.

What is claimed is:

1. A process for separating a mixture of gaseous components in which an internal gas flow is pumped through a plurality of beds in fluid commnunication in a series, each bed containing a pressure-dependent adsorbent packing, said mixture including a most highly adsorbed component and a less highly adsorbed component, said process being cyclical in nature such that:

(a) at the beginning of a cycle all of said beds except the one in a most downstream position with respect to said internal gas flow are at operating pressure at which said packing is an effective and selective adsorbent for said mixture, and said most downstream position bed is at a lower pressure at which relatively little gas is adsorbed and, (b) during said cycle, pumping gas from the most upstream of said beds to generate said internal gas flow and displace gas through said series in the downstream direction, withdrawing a first outlet flow of gas from a first outlet port in fluid communication with said most upstream bed, said first outlet flow consisting primarily of said most highly adsorbed component, and adding a feedstock flow of said mixture to said series of beds through an inlet port downstream from said first outlet port and separated from it by at least one bed, and withdrawing a second outlet flow from a second outlet port, said second outlet port being in fluid commnunication with the most downstream positioned bed in said series and separated from said inlet port by at least one bed, said second outlet flow consisting primarily of said less highly adsorbed component, such that, (c) by the end of said cycle the pressure in said most downstream position bed is increased to said operating pressure while the pressure in said most upstream bed is reduced to said lower pressure and, (d) at the end of said cycle, switching the positions of said ports among said plurality of beds such that each bed effectively advances upstream with respect to said internal gas flow by one position, except for said most upstream bed which is effectively moved to said most downstream position, said series including at least one simulated moving chromatographic column, located between said inlet port and said first outlet port.

2. The process according to claim 1 wherein said mixture is air and said highly adsorbed component is nitrogen.

3. The process of claim 2 wherein said simulated moving chromatographic column moves in increments that do not exceed ⅓ of said column.

4. The process according to claim 1 wherein said mixture to be separated is a mixture primarily of oxygen and argon.

5. A process for separating a mixture of gases, including the steps of:

(a) inducing, by pressure swing, both desorption and the flow of gas through at least one simulated moving chromatographic column packed with an effective and selective adsorbent for said mixture, (b) withdrawing a first outlet flow of gas from a first outlet port located upstream, with respect to said flow of gas, of an inlet port through which said mixture is admitted to said process, and (c) withdrawing a second outlet flow of gas from a second outlet port located downstream of said inlet port, wherein the most highly adsorbed component of said mixture is the primary product to be purified, said simulated moving chromatographic column is upstream of said inlet port, and said primary product is drawn from said process as said first outlet flow from a location upstream of said simulated moving chromatographic column.

6. The process according to claim 5 wherein said process is substantially continuous.

7. The process according to claim 6 wherein said mixture is air.

8. The process according to claim 5 wherein said simulated moving column moves in increments that do not exceed ⅓ of said column.

9. The process according to claim 8 wherein said mixture is air.

10. The process according to claim 5 wherein said flow of gas is induced through two simulated moving chrematographic columns in series.

11. The process according to claim 10 wherein said mixture is air.

12. The process according to claim 10 wherein said mixture is primarily of oxygen and argon.

* * * * *